(12) United States Patent
Korpela et al.

(10) Patent No.: US 7,326,684 B2
(45) Date of Patent: Feb. 5, 2008

(54) PEPTIDES FOR ENHANCING RESISTANCE TO MICROBIAL INFECTIONS

(76) Inventors: Timo Kalevi Korpela, Kraatarinkatu 1 D 42, Turku (FI) FIN-20610; Elena Navalotskaya, District G-9, fl. 72, Pushchino (RU) 142290; Tatiana Zargarova, District AB-23, fl 10, Pushchino (RU) 142290; Vladimir Zavialov, Ul. Zavodskaya 10 fl 12, Lyubuchany (RU) 142380

( * ) Notice: Subject to any disclaimer, the term of this patent is extended or adjusted under 35 U.S.C. 154(b) by 323 days.

(21) Appl. No.: 10/502,306

(22) PCT Filed: Jan. 21, 2003

(86) PCT No.: PCT/FI03/00044

§ 371 (c)(1),
(2), (4) Date: Feb. 7, 2005

(87) PCT Pub. No.: WO03/061683

PCT Pub. Date: Jul. 31, 2003

(65) Prior Publication Data

US 2005/0143293 A1 Jun. 30, 2005

(30) Foreign Application Priority Data

Jan. 23, 2002 (FI) .................................. 20020121

(51) Int. Cl.
*A61K 38/12* (2006.01)

(52) U.S. Cl. ......................................... 514/11; 530/317
(58) Field of Classification Search ...................... None
See application file for complete search history.

(56) References Cited

OTHER PUBLICATIONS

Zav'yalov, et al., Immunology letters, 1996, 49, 21-26.*
Navalotskaya, Elena et al. 2002. Synthetic peptide SLTCLVKGFY.. Peptides (23) pp. 1115-1119.
Navalotksaya, Elena et al. 2001. Synthetic Beta-endorphin-like peptide Peptides (22) pp. 2009-2013.

* cited by examiner

*Primary Examiner*—Anish Gupta
*Assistant Examiner*—Satyanarayana R. Gudibande
(74) *Attorney, Agent, or Firm*—Dodds & Associates; John Dodds; Susanne Somersalo

(57) ABSTRACT

The present invention is related to novel bioactive pentapeptides, pentarphins, the main indication of which is enhancing phagocytic activity of macrophages against microbes. In particular, the cyclopentapeptide, cyclo(Val-Lys-Gly-Phe-Tyr), termed cyclopeptarphin, was 100 times more active than tuftsin. Cyclopentarphin was non-toxic even at concentrations 1000 times higher than the minimum active dose, while being non-immunogenic. Furthermore, cyclopentarphin is more stable to enzymatic cleavage in vitro as compared to linear pentarphin and tuftsin and, hence, its life span in vivo is also larger than that of linear peptides. High efficacy and safety of cyclopentarphin enable elaboration of novel drugs that enhance the resistance of human and animal organisms to microbes and micro particles.

6 Claims, 2 Drawing Sheets

|                       |   |   |
|---|---|---|
| | 1     5 | |
| [Met⁵]Enkephalin | YGGFM | |
| | 1              10                20                30 | |
| Endorphin | YGGFMTSEKSQTPLVTLFKNAIIKNAYKKGE | |
| | 364                  377 | |
| HuIgG H-chain(364-377) | -SLTCLVKGFYPSDI- | |
| | 1              10 | |
| Immunorphin | SLTCLVKGFY | |
| | 1     5 | |
| Pentarphin | VKGFY | |

Figure 1

PEPTIDES FOR ENHANCING RESISTANCE TO MICROBIAL INFECTIONS

This is national stage application under 35 U.S.C. section 371 of international application WO 03/061683 filed on Jan. 23, 2003 and published on Jul. 31, 2003, said international application claiming priority of the Finnish national patent application FI20020000121 filed on Jan. 23, 2002.

FIELD OF INVENTION

The present invention is related to human and animal medicine, and more specifically, to improvement of the resistance of humans and animals to microbial infections and/or enhancement of the therapeutic effect of antibiotics. According to this invention, certain natural proteins contain peptide segments that can augment activity of macrophages and and other cells of immune system. These peptides can be used for the creation of novel drugs.

BACKGROUND OF INVENTION

A specific enzyme, leucokinase, that is located in the outer membrane of the neutrophils, spilits leucocinin, a leucophilic fraction of immunoglobulin G (IgG) and produces a phagocytosis-stimulating tetrapeptide (Najjar V. A. and Nishioka K., 1970, Nature 228, pp. 672-673). That tetrapeptide was subsequently named "tuftsin" (Najjar V. A. and Nishioka K., 1970, Nature 228, pp. 672-673; Sieminon I. Z. and Kluczyk A., 1999, Peptides 20, pp. 645-674). Tuftsin (Thr-Lys-Pro-Arg) is a 289-292 sequence in the $C_H2$ domain of the Fc subunit of human IgG1 heavy (H) chain. It was originally found that tuftsin stimulates phagocytosis after binding to polymorphonuclear cells (Constantopoulos A. and Najjar V. A., 1972, Cyobios. 6, pp. 97-100; Najjar V. A. and Constantopoulos A. A., 1972, J. Reticulendothel. Soc. 12, pp. 197-215; Najjar V. A., 1979, Clin. Wochenschr. 57, pp. 751-756; Najjar V. A., 1980, Adv. Exp. Med. Biol. 121 A, 131-147; Najjar V. A., 1983, Ann. NY Acad. Sci. 419, pp. 1-11). Subsequently, tuftsin was also shown to stimulate the phagocytosis activity of monocytes-macrophages (Coleman D. L., 1986, Eur. J. Clin. Microbiol. 5, pp. 1-5). Potentially, tuftsin could be used as a drug component to increase phagocytosis activities. However, the drawback is that tuftsin activity is very low demanding its high concentrations in blood circulation. Another drawback is that half-lives of linear peptides in blood are short.

In 1980 the existence of a β-endorphin-like sequence in $C_H3$ domain of the Fc subunit of human IgG1-4H-chain was reported (Julliard J. H. et al., 1980, Science 208, pp. 183-185). To isolate ACTH and β-endorphin from human placenta, the authors used immobilized antibodies to these hormones as affinity absorbents. A 50 kDa protein was thereby isolated and found to be an H-chain of IgG. Elucidation of the origin of such an effect led to the discovery of ACTH- and β-endorphin-like sequences in the H-chain. It was found that the human IgG1 H-chain fragment 364-377 (SLTCLVKGFYPSDI (SEQ ID NO:1); see FIG. 1) was 40% homologous to βendorphin fragment 10-23 (SQTPLVTLFKNAII (SEQ ID NO:2)). An artificial peptide (14 amino acid residues) corresponding to the β-endorphin-like human IgG1 sequence was synthesized and found to interact with rat brain receptors for β-endorphin (Houck J. C. et al., 1980, Science 207, 78-80). Our group synthesized a decapeptide SLTCLVKGFY(SEQ ID NO:3) (termed immunorphin) corresponding to the human IgG1 H-chain sequence 364-37. It was demonstrated to compete with [$^{125}$I]β-endorphin for high-affinity receptors on murine peritoneal macrophages ($K_i$=2.5 nM; Zav'yalov V. P. et al., 1996, Immun. Lett. 49, 21-26). Later on it was also demonstrated to compete with [$^{125}$I]β-endorphin for high-affinity receptors on T lymphocytes from the blood of healthy donors ($K_i$=0.6 nM). Tests of the specificity of the receptors revealed that they are insensitive to an antagonist of opioid receptors naloxone and [Met$^5$]enkephalin, i.e. they are non-opioid receptors. The displacement assays demonstrated that pentapeptide VKGFY(SEQ ID NO:4), termed hereinafter as pentarphin, was the shortest immunorphin fragment, capable of inhibiting [$^{125}$I]β-endorphin binding to non-opioid receptors on murine macrophages ($K_i$=12 nM) and human T lymphocytes ($K_i$=15 nM). According to the present invention, the primary effect of pentarphin, following binding to specific cell surface receptors, consists of the stimulation of the functions of macrophages and T lymphocytes.

BRIEF DESCRIPTION OF DRAWINGS

FIG. 1. Comparison of amino acid sequences of [Met$^5$] enkephalin (SEQ ID NO:11), β-endorphin (SEQ ID NO:10), β-endorphin-like fragments of human immunoglobulin GI (HuIgG1) heavy (H) chain (SEQ ID NO:1), immunorphin (SEQ ID NO:3), and pentarphin (SEQ ID NO:4).

DETAILED DESCRIPTION OF THE INVENTION

Figure 2:
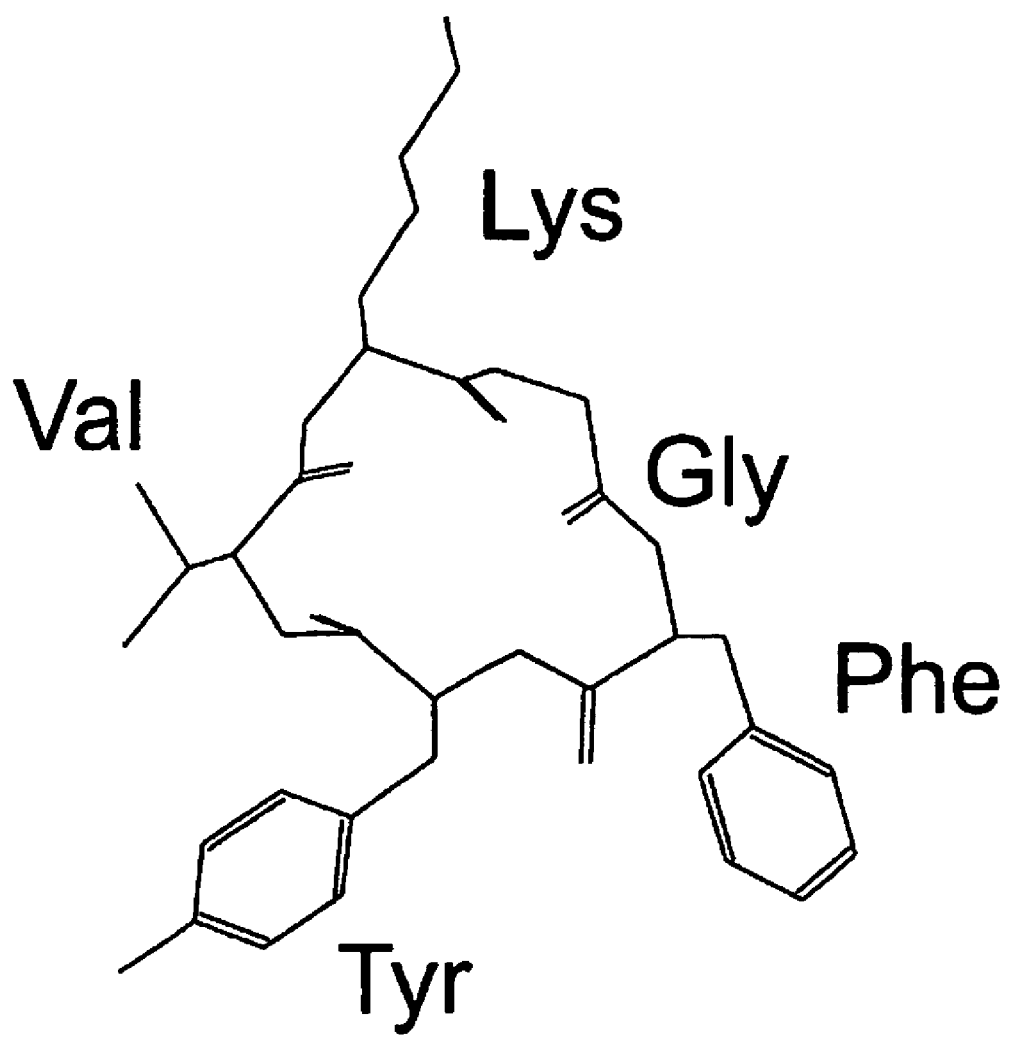
FIG. 2. Structure of cyclopentarphin.

The present invention is related to novel bioactive compounds—pentapeptide Val-Lys-Gly-Phe-Tyr (SEQ ID NO:4, and its cyclic analog—cyclo(Val-Lys-Gly-Phe-Tyr), capable of enhancing phagocytic activity of mouse peritoneal macrophages against virulent bacterial strains and of binding to a variety of cells of immune system. The term pentarphin is used hereafter for the linear sequence described above. In a larger meaning the term pentarphins is used for the linear or cyclic sequences or for sequences containing mentioned sequences within their molecule and having related biological activities as the linear or cyclic pentarphin.

According to this invention, during phagocytosis pentarphins bind to the specific high-affinity receptors on macrophage surface and enhance the capacity of phagocytic cells to digest captured microbes. However, for example, a virulent bacterium *Salmonella typhimurium* has adapted, as many other virulent microorganisms, in the process of natural selection, to protect themselves against the bactericidal action of phagocytes. Such adapted microbes release in the surrounding medium so-called "virulence factors" that interfere with the process of formation of a junction between phagosomes (bubbles formed by cell membrane that contain captured microbes) and lysosomes. As a result, phagolysosomes are not formed and lysosomal enzymes have no access to microbes and therefore cannot digest them. Data presented in Table 1 show that in the absence of pentarphins (control) captured microorganisms were not digested but, in contrast, propagated themselves inside phagocytes (PN increases from 10.17±0.18 to 15.50±0.34 between 2 and 7 h of phagocytosis). Pentarphin and cyclopentarphin do not influence viability and growth of *S. typhimurium*, that is, they are not peptides-antibiotics. Similar to tuftsin, both peptides stimulate the capacity of phagocytes to digest captured microorganisms.

Pentarphins have following advantages as compared to classical antibiotics:

1. Unlike antibiotics that act directly on microorganism, pentarphins affect phagocytes stimulating their digestive function. Therefore, the activator peptides can be effective in microbial infections, i.e. to be universal antimicrobial agents.
2. Antibiotics are toxic and cause a number of undesirable side effects (allergy, disbacteriosis, changes in blood cellular content, impairments of liver, kidney and the central nervous system functions etc.). Pentarphins are non-toxic, since the products of their hydrolysis are natural amino acids, while the only effect is the stimulation of the immune system.

Antibiotics are widely used, commercially important drugs for treatment of a multitude of infectious diseases of human and higher animals. However, antibiotics have severe drawbacks for their toxicity, narrow effective dose range, and various side effects. Therefore, it is propitious to try to increase their activities by other means. High efficacy and safety of pentarphins form the basis for elaboration of novel effective therapeutic agents that enhance the resistance of human and animal organisms to pathogenic microbes or other microparticles eliminated by macrophages. In addition, it appeared promising to work out combined preparations of pentarphins and antibiotics. The combinatory drugs influence microbe and macrophage simultaneously. Such an approach will allow therapeutic doses of antibiotics and consequently their toxicity to be significantly reduced, whereas antimicrobial activity of preparation as a whole to be significantly increased.

In this invention, it has been shown that certain favourable physiological effects of antibiotics can be amplified by biologically active peptides, preferably cyclopeptides, corresponding to the β-endorphin-like sequences of human IgG1-4 subclasses. The mentioned cyclopeptides can be commercially produced by synthetic techniques. The present invention provides definite improvement of drugs based on antibiotics designed for treatment of humans and animals. The peptide parts of such drugs include the biologically active cyclopeptides corresponding to the β-endorphin-like sequence of IgG subclasses of different animal species. Although it was impossible to test experimentally all the potentially bioactive peptide structures, such structures were revealed by extensive comparisons of available amino acid sequences of IgG subclasses from different species by computer and molecular modeling techniques taking into account the data on the localization of the β-endorphin-like sequence of human IgG1-4 subclasses and the experimental data on the competition of pentarphin with [125I]β-endorphin for the common receptors. Therefore the present invention is not limited to the linear or cyclic structure of pentapeptide VKGFY (SEQ ID NO:4) but also includes related structures from other animals with the same biological effects, i.e. the capability to enhance the activity of macrophages and/or bind to immunocompetent cells. It is reasonable to assume that in the process of natural selection the changes in the amino acid sequence of the pentarphin-like site of IgG were selected not to abolish the biological activities of the site. Consequently, all peptides corresponding to this site in all IgG subclasses of different species might reproduce the activity of pentarphin.

To test a synergy between antibiotics and pentarphins, we employed the classic macrophage assays with mouse peritoneal macrophages in a cell culture system. The cell culture conditions are strongly reminiscent of that of blood circulation. In fact, in cell cultures, which are commonly used for testing of potential drugs, the conditions are strictly maintained similar to the blood circulation as to the temperature, pH, buffer, minerals, $CO_2$- and $O_2$-partial pressures, and so on. Thus, it is highly predictable that the biologically active compositions of the present invention can be used as medical drugs for humans and animals. Such effective drugs are very desirable for treatment persons with a lowered resistance to microbial infections like those having different kinds of immunodeficiency, for example, AIDS.

It was demonstrated that pentarphins (see Example 4) have very low or no toxicity, because of their amino acid nature. On the other hand, they are not immunogenic. Therefore they are extremely suitable components for any drug formulations. For certain purposes derivatives of pentarphins may be useful. Larger pentarphin polymers (repeated polypeptide sequences) will possibly be immunogenic. However, such polymers or derivatives may possess relatively higher activity, which can make their usage favorable.

The role of macrophages is essentially to remove extremely small foreign particles, for example microbial cells, from the organism. The present invention indicates that this process can be accelerated by pentarphins. One would expect that macrophages activated so would also remove other particles from human and animal blood circulation, thus having a beneficial effect on, for instance, allergic reactions.

It is theoretically predictable that the peptides and their fragments, according to the present invention, will be useful for amelioration of allergic reactions, because the mentioned peptides activate T cells. Allergic reactions are mediated by activated B cells as well as interleukin-4-secreting T ($T_{H2}$) cells; this cytokine is necessary for IgE production by B cells. There are literature data concerning role of β-endorphin in the regulation of cytokine production by T cells: β-endorphin stimulates IL-2, IL-4 and Y-interferon production by murine $CD4^+$ T cells (van den Bergh P. et al., 1994, Cell. Immunol. 154 109-122; van den Bergh P. et al., 1994, Lymphokine Cytokine Res., 13, 63-69). It was shown that β-endorphin could modulate the magnitude of an IL-4 induced IgE response (Aebisher I. 1996, Exp. Dermatol., 5, 38-44).

The present invention shows that pentarphins and certain other peptides have sequence homologies (see FIG. 1). All these peptides have strong physiological effects on animal and human organisms. According to this invention, at least macrophages and T-lymphocytes have receptors for pentarphins. Both of these cells are crucial for organism's resistance against microbial attacks. T-cell activation takes place at the first stage of the development of specific immune response to infection. Antigen-primed naive T cells differentiate into either helper cells ($T_{H2}$) or inflammatory cells ($T_{H1}$). $T_{H2}$ cells participate in the development of humoral immunity (production of specific antibodies) and $T_{H1}$ cells take place in macrophage activation. Immunorphin and its fragments are not species-specific, since our results show that these peptides bind with high affinity to specific receptors on both mouse and human cells. Immunorphin is a fragment of the constant part of the heavy chain of IgG. This fragment has the same sequence at least in human, mouse, and rat IgG.

Numerous methods of preparing drug formulations in the context of peptide drugs, including tuftsin, have been described in literature (see, for example, U.S. Pat. No. 4,816,560, EP0448811, EP0253190). High tolerance of cyclopentarphin to the action of proteolytic enzymes enables its administration not only intramuscularly but also per os and in nosal. According to the present invention, it is possible to find out appropriate formulations using pentarphins alone as effective substances, or combinations of pentaprphins with antibiotics, such as penicillins, cefalosporins, tetracyclins, streptomycins, laevomycetins, polymyxins, rifamycins, peptide antibiotics (exemplified by gramicidins, bacitracins, and polymycsins).

It is evident that pentarphins structure (5-residue peptide, minimal) forms the very basis of the present invention. With the knowledge described in this invention, it is possible to design many other active structures. For example, it is possible to create polymeric forms of pentarphins with or without using synthetic or biological linker molecules between the active units. Further, it is possible to add flanking sequences outside of N- and C-terminal ends, or to add such ones to the amino acid side chains (to the Lys residue) to change solubility etc. It is also possible to prepare macromolecular carriers with one or more active peptides linked to them.

In the following the invention is further illustrated by non-limiting examples.

EXAMPLE 1

Pentarphins and Immunorphins Activate Cells of Immune System (3-[$^{125}$I]iodotyrosyl$^{27}$)β-endorphin (~2000 Ci/mmol specific activity) was purchased from Amersham (UK). Na$^{125}$I (2×10$^6$ Ci/M specific activity) was from Russian Scientific Center "Applied Chemistry" (St. Petersburg, Russia). All media, sera for culturing cells, 1,3,4,6-tetra-chloro-3α,6α diphenyl glycoluril (Iodogen) and other chemicals were obtained from Sigma (St. Louis, Mo.). The decapeptide encompassing the sequence 364-373 of HuIgG (immunorphin) and its fragments were synthesized by using pentafluorophenyl ethers of N-protected amino acids. The peptides were purified by HPLC followed by fast atom bombardment mass spectrometric analysis. Only peptides that were >95% pure were used.

Mononuclear cells were separated from healthy donors blood according to the Boyum method. T lymphocytes were purified by a nylon wool column filtration method. The non-adherent fraction was eluted with RPMI-1640 medium supplemented with 5% heat-inactivated fetal calf serum. This fraction contained T lymphocytes and small amounts of monocytes and B lymphocytes.

The binding of [$^{125}$I]β-endorphin to T lymphocytes was measured as follows: 10$^6$ cells per tube were incubated with labeled peptide at a concentration of 10$^{-7}$-10$^{-11}$ M for 1 h at 4° C. in 1 ml RPMI-1640 medium containing 20 mM NaN$_3$ and 10 mM Hepes, pH 7.5. The incubation was terminated by rapid filtration through GF/A glass fiber filters (Whatman, UK) under vacuum pressure. Filters were rinsed twice with 5 ml volumes of ice-cold 0.15 M NaCl. The cell-bound radioactivity was measured using $^{121}$I Minigamma counter (LKB, Sweden). Non-specific binding of [$^{125}$I]β-endorphin was measured in the presence of 10 μM unlabeled β-endorphin. The equilibrium dissociation constant ($K_d$) was estimated by Scatchard analysis.

Immunorphin (10 μg) and the peptide H-VKGFY-OH (SEQ ID NO:4) (10 μg) were labeled by solid phase oxidation method using Iodogen and Na$^{125}$I (1 mCi). The labeled peptides were purified by gel filtration on Sephadex G-10 (0.9×10 cm column, 0.05 M phosphate buffer, pH 7.5). The purity of the labeled peptides was tested by thin-layer chromatography on aluminium oxide glass with n-butano/acetic acid/water (4:1:1) solvent system, followed by autoradiography. The specific activity of [$^{125}$I]-immunorphin and [$^{125}$I]-H-VKGFY-OH were 232 Ci/mmol and 179 Ci/mmol respectively. Assay of [$^{125}$I]-immunorphin (10$^{-10}$-10$^{-7}$ M) and [$^{125}$I]-H-VKGFY-OH (10$^{-10}$-10$^{-7}$ M) binding to T lymphocytes (10$^6$ cells per tube) was carried out in 1 ml RPMI-1640 medium containing 10 mM Hepes, 20 mM NaN$_3$, and 0.6 mg/L PMSF, pH 7.4 at 4° C. for 40 min. The reaction mixture was then filtered through GF/A filters (Whatman, UK). Filters were rinsed twice with 5 ml volumes of ice-cold 0.15 M NaCl, pH 7.4. Radioactivity was counted using 1211 Minigamma counter (LKB). Non-specific binding of the labeled peptide was measured in the presence of 10 μM of the unlabeled peptide.

To test the inhibitory effect of unlabeled naloxone, Met-enkephalin, and immunorphin fragments on the binding of [$^{125}$I]β-endorphin, T lymphocytes (10$^6$ cells per tube) were incubated with 1 nM [$^{125}$I]β-endorphin and unlabeled ligands at various concentrations (10$^{-10}$-10$^{-6}$ M) as described in Section 2.4. The results were plotted as percentage of specific binding vs. log of competitor concentration, and IC$_{50}$ values were determined graphically. The inhibition constant ($K_i$) was calculated according to the equation:

$$K_i = IC_{50}/(1+[L]/K_d),$$

where [L] is a molar concentration of [$^{125}$I]β-endorphin, $K_d$ is the dissociation constant of [$^{125}$I]β-endorphin/receptor complex, and IC$_{50}$ is the concentration of the competing ligand causing half-maximum displacement of [$^{125}$I]β-endorphin. β-Endorphin was found to interact specifically with T lymphocytes separated from normal human blood. The data propose the presence of one class binding sites with the $K_d$ value of 0.25±0.03 nM. Non-specific [$^{125}$I]β-endorphin binding that occurs in the presence of 10 μM unlabeled β-endorphin constitutes about 11% of the total binding value.

To examine the specificity of the β-endorphin binding sites, competition experiments were performed using the constant concentration of [$^{125}$I]β-endorphin and increasing concentrations of unlabeled ligands (naloxone, Met-enkephalin, immunorphin and eight synthetic immunorphin fragments with various chain lengths; see section 2.5 of the previous part). Displacement curves indicated that only six unlabelled peptides (H-VKGFY-OH (SEQ ID NO:4), H-LVKGFY-OH (SEQ ID NO:5), H-CLVKGFY-OH (SEQ ID NO:6), H-TCLVKGFY-OH (SEQ ID NO:7), H-LTCLVKGFY-OH (SEQ ID NO:8) and immunorphin) were able to compete with [$^{125}$I]β-endorphin for the same binding sites. The $K_i$ values correlate with ligand-receptor affinity and inhibiting potential of ligands. The results of the displacement assay demonstrated that β-endorphin binding to this type of receptors is not inhibited by naloxone and Met-enkephalin. A minimum fragment of immunorphin retaining its inhibitory activity in the competition test was found to be the pentapeptide H-VKGFY—OH (SEQ ID NO:4). The pentapeptide was characterized by lesser inhibiting capacity ($K_i$=15 nM) as compared to immunorphin (0.6 nM) and its longer fragments (H-LVKGFY-OH (SEQ ID NO:5), $K_i$=8.0 nM; H-CLVKGFY-OH (SEQ ID NO:6), $K_i$=3.4 nM; H-TCLVKGFY-OH (SEQ ID NO:7), $K_i$=2.2 nM; H-LTCLVKGFY-OH (SEQ ID NO:8, $K_i$=1.0 nM). Thus, the β-endorphin receptors expressed by T lymphocytes are highly specific and naloxone-insensitive ones.

The Scatchard plots demonstrate the specific binding of [$^{125}$I]-immunorphin to T lymphocytes in the absence (plot 1; $K_d$=7.0±0.3 nM) and in the presence (plot 2; $K_d$=7.4±0.2 nM) of naloxone. The results of this experiment confirmed that naloxone does not influence the kinetic of [$^{125}$I]-immunorphin binding to the receptors on T lymphocytes.

The displacement assays demonstrated that pentapeptide H-VKGFY-OH (SEQ ID NO:4) was the shortest active immunorphin fragment. We prepared [$^{125}$I]-H-VKGFY-OH and studied its interaction with T lymphocytes. Scatchard analysis of the binding showed that the data best fit a one-site model. The $K_d$ value for [$^{125}$I]-H-VKGFY-OH/receptor complex was 36.3±0.5 nM. Non-specific binding of the labeled peptide to T lymphocytes was about 8% of its total binding to these cells.

The results of the binding assays confirmed that lymphocytes separated from normal human blood express high affinity binding sites for β-endorphin, $K_d$=(0.25±0.03) nM. The binding of β-endorphin to these sites was naloxone- and Met-enkephalin-insensitive, but sensitive to immunorphin and its fragments H-VKGFY-OH (SEQ ID NO:4), H-LVKGFY-OH (SEQ ID NO:5), H-CLVKGFY-OH (SEQ ID NO:6), H-TCLVKGFY-OH (SEQ ID NO:7), H-LTCLVKGFY-OH (SEQ ID NO:8) (Tab. 1). Thus, T lymphocytes from normal human blood express non-opioid receptors for β-endorphin.

Immunorphin (H-SLTCLVKGFY-OH(SEQ ID NO:3)) is homologous (50%) to the β-endorphin fragment $10^{-19}$ (SQTPLVTLFK)(SEQ ID NO:9). The high affinity binding of immunorphin ($K_d$=7.0±0.3 nM) and its fragment H-VKGFY-OH(SEQ ID NO:4) ($K_d$=36.3±0.5 nM) to non-opioid receptors for β-endorphin on T lymphocytes shows that α-endorphin is a peptide with a dualistic nature: its C-terminal moiety binds to non-opiod receptors, whereas its N-terminal enkephalin sequence is responsible for β-endorphin binding to opioid receptors. Therefore, pentarphins can have a special function in organisms which is related to certain functions of β-endorphin. We have found that β-endorphin, immunorphin and pentarphin stimulate Con A-induced proliferation of T lymphocytes from the blood of healthy donors. [Met$^5$]enkephalin and an antagonist of opioid receptors naloxone, tested in parallell, were not active. The stimulating effect of β-endorphin, immunorphin and pentarphin on T lymphocyte proliferation was not inhibited by naloxone. Thus, these peptides bind to common naloxone-insensitive binding sites on T lymphocytes and enhance Con A-induced proliferation of these cells.

EXAMPLE 2

Phagocytosis of *S. typhimurium* by Macrophages in the Absence or in the

Presence of Pentarphin, Cyclopentarphin, and Tuftsin

Pentarphin was obtained by a solid-phase synthesis. The crude product was purified by HPLC on a Zorbax ODS column (4×150 mm, 5 μm particle size) using linear gradient of water acetonitrile (95%) in 0.2% TCA (10-25%, 20 min) at a flow rate of 1 ml/min. According to the absorbance at 220 nm, the main substance (pentarphin) content was 98%. The peptide structure was confirmed by an amino acid analysis under standard conditions with a D500 amino acid analyzer (Durrum, USA). Molecular mass of pentarphin was estimated by mass spectrometric analysis using Vision 2000 spectrometer ("Thermo Bioanalysis", Great Britain).

Cyclopentarphin was obtained by the cyclization reaction of linear pentarphin (having the side chain groups protected) through amino group of Val to an activated carboxyl group of Tyr. The reaction product was unmasked from protective groups and purified by HPLC as described above. The molar yield was 15%. Mass spectrometric analysis showed the molecular peak of cyclopentarphin (594 Da) in the spectrum.

Peritoneal macrophages were isolated from CBA mice (16-18 g). The virulent strain *Salmonella typhimurium* 415 with typical morphological and functional properties was used. $LD_{50}$ was approximately 100 microbial cells injected intraperitoneally into white mice. *S. typhimurium* was grown in Hottinger's broth for 4-6 h at 37° C., then transferred to beef-extract agar and incubated at 37° C. for 18 h. Macrophage monolayers on cover glasses were cultivated in sterile test tubes in 199 medium supplemented with streptomycin and penicillin (100 μg/ml each) and inactivated fetal calf serum (5%) at 37° C. 24 h later macrophages were infected with 199 medium supplemented with serum and *S. typhimurium* 415 (108 microbial cells/ml final concentration). Microorganisms and peptides (tuftsin, pentarphin, or cyclopentarphin) at particular concentrations were added to the cultivation medium simultaneously. In 2 h the contact between microbes and macrophages was interrupted by replacing the infection medium with a fresh one supplemented with antibiotics. To prevent the recapture of bacteria released from destroyed phagocytes by other cells, cultivation medium was replaced with a fresh one every two hours. Macrophages on cover glasses (in triplicate for every time point, namely 1,2,4,7 and 12 h) were fixed in methanol for 7 min. After that, the preparations were stained with 0.1% azur II-eosin water solution for 5 min. Cells (300 per cover glass) were examined using light microscope and analyzed for following parameters: phagocytic activity (PA)—a percentage of macrophages, participating in phagocytosis; bacterial cytocidal activity (BCA)—a percentage of phagocytes, destroyed by intracellular bacteria; and phagocytic number (PN)—an average number of microbes per macrophage.

The values of the main characteristics (PA, PN, BCA) of *S. typhimurium* phagocytosis in the absence (control) or in the presence of pentarphin (1 nM), cyclopentarphin (1 nM) and tuftsin (100 nM) are shown in Table 1. BCA in control was more than 65% within 7h, and within 12 h all macrophage monolayer was destroyed by intracellular microorganisms. The presence of 1 nM pentarphin or cyclopentarphin in cultivation medium resulted in a significant increase in bactericidal activity of macrophages. In the presence of pentarphin, phagocytes completely digested the captured microbes within 12 h, and in the presence of cyclopentarphin—within 7 h of phagocytosis. Tuftsin acted the same way at a concentration of 100 nM, that is, its activity was 100 times lower. Thus, pentarphin enhances the bactericidal activity of peritoneal macrophages in relation to *S. typhimurium* 415, in its presence at a concentration of 1 nM, phagocytosis of this bacteria in vitro completes with total digestion of captured microbes. Cyclopentarphin is preferable in a drug composition, because its half-life in biological fluids is considerably longer than its linear analogs, as known from prior art.

EXAMPLE 3

Combined Action of Pentarphin and Streptomycin

Macrophage monolayers on cover glasses were cultivated and infected as described above in Example 1. Microorganisms, streptomycine and peptides (pentarphin, or cyclopentarphin) at particular concentrations were added to the cultivation medium simultaneously. In 2 h, the contact between microbes and macrophages was interrupted by replacing the infection medium with a fresh one supplemented with antibiotics. Macrophages on cover glasses (in triplicate for every time point, namely 1, 2, and 4 h) were fixed in methanol for 7 min. After that, the preparations were stained with 0.1% azur II-eosin water solution for 5 min. Cells (300 per cover glass) were examined under a light microscope and analyzed for following parameters: phagocytic activity (PA)—a percentage of macrophages, participating in phagocytosis; bacterial cytocidal activity (BCA)—a percentage of phagocytes, destroyed by intracellular bacteria; and phagocytic number (PN)—an average number of microbes per macrophage. The data given in Table 2 show that the combined action of streptomycine (10 µg/ml) иpentarphin (1 nM) allows the antibiotic dose to be lowered 5 times.

EXAMPLE 4

Toxicity and Immunogenicity of Pentarphin and Immunorphin

The toxicity of pentarphin and immunorphin was estimated by intraperitoneal injection of peptides (10, 100, 250, 1000, 2500, and 3000 mg/kg of body weight) to BCA mice (16-18g). The $LD_{50}$ value was 2500 mg/kg for each peptide, i.e. this dose is not physiological. Active concentrations of both peptides are 10-100 µg/kg. Very low toxicity of the peptides can be attributed to the fact that aminoacids are the only degradation products of these compounds.

No immunogenicity was observed during several experiments with pentarphin and immunorphin utilizing mice as model animals. This was an expectable result, because the related peptides, Met-enkephalin and Leu-enkephalin, are known to be nonimmunogenic. In general, small peptides do not induce antibody production.

TABLE 1

Effect of cyclopentarphin, pentarphin and tuftsin on digestion of the virulent bacterial strain S. typhimurium 415 by mouse peritoneal macrophages in vitro.

| Peptide | Phagocytosis time, h | *PA, % ± SEM | **BCA, % ± SEM | ***PN, n ± SEM |
|---|---|---|---|---|
| Control | 1 | 65.33 ± 1.11 | 1.33 ± 0.67 | 3.90 ± 0.13 |
|  | 2 | 72.67 ± 1.07 | 13.67 ± 0.69 | 10.17 ± 0.18 |
|  | 4 | 62.33 ± 1.29 | 35.67 ± 1.41 | 11.17 ± 1.03 |
|  | 7 | 29.00 ± 0.89 | 66.67 ± 0.62 | 15.50 ± 0.34 |
|  | 12 | 0 | 100 | — |
| Pentarphin (1 nM) | 1 | 84.08 ± 2.12 | 1.08 ± 0.71 | 7.11 ± 0.15 |
|  | 2 | 89.15 ± 1.78 | 1.55 ± 0.65 | 9.29 ± 0.74 |
|  | 4 | 66.82 ± 1.14 | 9.32 ± 1.32 | 6.02 ± 0.66 |
|  | 7 | 23.31 ± 0.84 | 10.24. ± 1.17 | 1.03 ± 0.24 |
|  | 12 | 3.73 ± 0.64 | 2.35 ± 1.21 | 0.66 ± 0.12 |
| Cyclopentarphin (1 nM) | 1 | 87.81 ± 3.14 | 1.25 ± 0.64 | 7.78 ± 0.39 |
|  | 2 | 91.33 ± 2..19 | 1.06 ± 0.49 | 8.81 ± 0.27 |
|  | 4 | 57.43 ± 2.01 | 2.13 ± 0.60 | 5.32 ± 0.51 |
|  | 7 | 1.74 ± 0.44 | 2.22 ± 1.31 | 0.27 ± 0.20 |
| Tuftsin (100 nM) | 1 | 66.07 ± 1.82 | 1.41 ± 0.27 | 5.84 ± 0.27 |
|  | 2 | 74.11 ± 1.42 | 8.12 ± 0.99 | 7.31 ± 0.25 |
|  | 4 | 61.97 ± 1.18 | 29.34 ± 0.75 | 6.29 ± 0.48 |
|  | 7 | 38.48 ± 0.23 | 31.46 ± 1.23 | 3.32 ± 0.56 |
|  | 12 | 9.31 ± 0.29 | 7.64 ± 1.38 | 1.36 ± 0.86 |

*PA—phagocytic activity, a percentage of macrophages, participating in phagocytosis;
**BCA—bacterial cytocidal activity, a percentage of phagocytes, destroyed by intracellular bacteria;
***PN—phagocytic number, an average number of microbes per macrophage.

TABLE 2

Effect of streptomycine + pentarphin on the digestion of the virulent bacterial strain S. typhimurium 415 by mouse peritoneal macrophages in vitro.

| Peptide | Phagocytosis time, h | PA, % ± SEM | BCA, % ± SEM | PN, n ± SEM |
|---|---|---|---|---|
| Streptomycine (50 µg/ml) | 1 | 86.45 ± 2.13 | 1.04 ± 0.32 | 8.56 ± 0.76 |
|  | 2 | 96.17 ± 1.76 | 1.12 ± 0.74 | 2.03 ± 0.46 |
|  | 4 | 0 | 0 | 0 |
| Streptomycine (10 µg/ml) + pentarphin (1 nM) | 1 | 87.65 ± 2.19 | 0.94 ± 0.49 | 8.60 ± 0.58 |
|  | 2 | 98.22 ± 1.94 | 1.05 ± 0.54 | 2.11 ± 0.44 |
|  | 4 | 0 | 0 | 0 |
| Streptomycine (10 µg/ml) + cyclopentarphin (1 nM) | 1 | 91.66 ± 2.27 | 0.99 ± 0.56 | 8.92 ± 0.83 |
|  | 2 | 99.31 ± 2.44 | 1.17 ± 0.61 | 2.01 ± 0.39 |
|  | 4 | 0 | 0 | 0 |

The invention claimed is:

1. A pentarphin molecule consisting of a structure of cyclo (Val-Lys-Gly-Phe-Tyr) and further being called as cyclopentarphin.

2. A drug composition comprising pentarphin molecule in a cyclic form and said pentarphin molecule consisting of the amino acid sequence according to SEQ ID NO: 4.

3. The drug composition according to claim 2, wherein the composition additionally contains at least one conventional antibiotic.

4. The drug composition according to claim 3, wherein the conventional antibiotic is streptomycin.

5. A cell cultivation medium for mammal cell cultivation, said cultivation further containing macrophages, said cultivation medium further comprising pentarphin molecules consisting of the amino acid sequence according to SEQ ID NO: 4 and having a cyclic structure at concentrations less than 10 mg/l.

6. The cell cultivation medium according to claim 5, wherein the medium additionally contains antibiotics.

* * * * *

SEQUENCE LISTING

<160> NUMBER OF SEQ ID NOS: 11

<210> SEQ ID NO 1
<211> LENGTH: 14
<212> TYPE: PRT
<213> ORGANISM: artificial
<220> FEATURE:
<223> OTHER INFORMATION: artificially synthetized peptide corresponding to human IgG1 H-chain frqagment 364-377

<400> SEQUENCE: 1

```
Ser Leu Thr Cys Leu Val Lys Gly Phe Tyr Pro Ser Asp Ile
1               5                   10

<210> SEQ ID NO 2
<211> LENGTH: 14
<212> TYPE: PRT
<213> ORGANISM: artificial
<220> FEATURE:
<223> OTHER INFORMATION: artificially synthetized peptide corresponding
      to human beta endorphin fragment 10-23

<400> SEQUENCE: 2

Ser Gln Thr Pro Leu Val Thr Leu Phe Lys Asn Ala Ile Ile
1               5                   10

<210> SEQ ID NO 3
<211> LENGTH: 10
<212> TYPE: PRT
<213> ORGANISM: artificial
<220> FEATURE:
<223> OTHER INFORMATION: artificially synthetized peptide corresponding
      to the human IgG1 H-chain sequence 364-373

<400> SEQUENCE: 3

Ser Leu Thr Cys Leu Val Lys Gly Phe Tyr
1               5                   10

<210> SEQ ID NO 4
<211> LENGTH: 5
<212> TYPE: PRT
<213> ORGANISM: artificial
<220> FEATURE:
<223> OTHER INFORMATION: artificially synthetized peptide corresponding
      to human IgG1 H-chain fragment 369-373

<400> SEQUENCE: 4

Val Lys Gly Phe Tyr
1               5

<210> SEQ ID NO 5
<211> LENGTH: 6
<212> TYPE: PRT
<213> ORGANISM: artificial
<220> FEATURE:
<223> OTHER INFORMATION: artificially synthetized peptide corresponding
      to human IgG1 H-chain fragment 368-373

<400> SEQUENCE: 5

Leu Val Lys Gly Phe Tyr
1               5

<210> SEQ ID NO 6
<211> LENGTH: 7
<212> TYPE: PRT
<213> ORGANISM: artificial
<220> FEATURE:
<223> OTHER INFORMATION: artificially synthetized peptide corresponding
      to human IgG1 H-chain fragment 367-373

<400> SEQUENCE: 6

Cys Leu Val Lys Gly Phe Tyr
1               5

<210> SEQ ID NO 7
<211> LENGTH: 8
<212> TYPE: PRT
<213> ORGANISM: artificial
<220> FEATURE:
```

```
-continued

<223> OTHER INFORMATION: artificially synthetized peptide corresponding
      to human IgG1 H-chain fragment 366-373

<400> SEQUENCE: 7

Thr Cys Leu Val Lys Gly Phe Tyr
1               5

<210> SEQ ID NO 8
<211> LENGTH: 9
<212> TYPE: PRT
<213> ORGANISM: artificial
<220> FEATURE:
<223> OTHER INFORMATION: artificially synthetized peptide corresponding
      to human IgG1 H-chain fragment 365-373

<400> SEQUENCE: 8

Leu Thr Cys Leu Val Lys Gly Phe Tyr
1               5

<210> SEQ ID NO 9
<211> LENGTH: 10
<212> TYPE: PRT
<213> ORGANISM: artificial
<220> FEATURE:
<223> OTHER INFORMATION: artificially synthetised peptide corresponding
      to human beta endorphin fragment 10-19

<400> SEQUENCE: 9

Ser Gln Thr Pro Leu Val Thr Leu Phe Lys
1               5                   10

<210> SEQ ID NO 10
<211> LENGTH: 31
<212> TYPE: PRT
<213> ORGANISM: human
<220> FEATURE:
<221> NAME/KEY: PEPTIDE
<222> LOCATION: (1)..(31)
<223> OTHER INFORMATION: Beta-endorphin

<400> SEQUENCE: 10

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 11
<211> LENGTH: 5
<212> TYPE: PRT
<213> ORGANISM: artificial
<220> FEATURE:
<223> OTHER INFORMATION: artificial peptide corresponding to human beta
      edonrphin fragment 1-5

<400> SEQUENCE: 11

Tyr Gly Gly Phe Met
1               5
```